United States Patent
Li et al.

(10) Patent No.: US 10,745,511 B2
(45) Date of Patent: Aug. 18, 2020

(54) HYDROPHILIC AND BIOLOGICALLY SAFE POLYMER FOAM AS WELL AS PREPARATION METHOD AND APPLICATION THEREOF

(71) Applicants: Jianli Zhang, Zhengzhou (CN); Qing Zhou, Zhengzhou (CN)

(72) Inventors: Mingying Li, Zhengzhou (CN); Jianli Zhang, Zhengzhou (CN); Qing Zhou, Zhengzhou (CN)

(*) Notice: Subject to any disclaimer, the term of this patent is extended or adjusted under 35 U.S.C. 154(b) by 0 days.

(21) Appl. No.: 15/888,022

(22) Filed: Feb. 3, 2018

(65) Prior Publication Data
US 2018/0155484 A1    Jun. 7, 2018

Related U.S. Application Data

(63) Continuation of application No. PCT/CN2016/092823, filed on Aug. 2, 2016.

(30) Foreign Application Priority Data

Aug. 4, 2015  (CN) .......................... 2015 1 0472222

(51) Int. Cl.
| | |
|---|---|
| *C08G 18/10* | (2006.01) |
| *C08G 18/08* | (2006.01) |
| *A61L 15/26* | (2006.01) |
| *C08G 18/32* | (2006.01) |
| *C08G 18/30* | (2006.01) |
| *C08G 18/48* | (2006.01) |
| *C08G 18/77* | (2006.01) |
| *A61L 15/42* | (2006.01) |
| *C08G 18/73* | (2006.01) |
| *C08G 101/00* | (2006.01) |

(52) U.S. Cl.
CPC .............. *C08G 18/14* (2013.01); *A61L 15/26* (2013.01); *A61L 15/425* (2013.01); *C08G 18/10* (2013.01); *C08G 18/302* (2013.01); *C08G 18/3206* (2013.01); *C08G 18/4829* (2013.01); *C08G 18/4837* (2013.01); *C08G 18/73* (2013.01); *C08G 18/771* (2013.01); *C08G 2101/0008* (2013.01); *C08G 2101/0066* (2013.01); *C08G 2101/0083* (2013.01); *C08J 2205/05* (2013.01); *C08J 2205/06* (2013.01); *C08J 2207/10* (2013.01); *C08J 2207/12* (2013.01); *C08J 2375/08* (2013.01)

(58) Field of Classification Search
CPC ....... A61L 15/26; A61L 15/425; C08G 18/10; C08G 18/14; C08G 18/30; C08G 18/302; C08G 18/3206; C08G 18/4829; C08G 18/4837; C08G 18/73; C08G 18/771; C08G 2101/0008; C08G 2101/0066; C08G 2101/0083; C08G 2205/05; C08J 2205/06; C08J 2207/10; C08J 2207/12; C08J 2375/08; C08L 75/04
See application file for complete search history.

(56) References Cited

U.S. PATENT DOCUMENTS

| | | | |
|---|---|---|---|
| 7,807,725 B2 | 10/2010 | Nguyen-Kim et al. | |
| 2006/0263324 A1 | 11/2006 | Nguyen-Kim et al. | |
| 2007/0149634 A1 | 6/2007 | Haider et al. | |
| 2009/0130174 A1* | 5/2009 | Guelcher .............. | A61K 31/74 424/426 |
| 2011/0171277 A1 | 7/2011 | Schonberger | |
| 2013/0131207 A1* | 5/2013 | Niesten .................. | A61L 15/26 521/174 |

FOREIGN PATENT DOCUMENTS

CN    105153393 A    12/2015

OTHER PUBLICATIONS

International Search Report of PCT/CN2016/092823, dated Oct. 10, 2016.

* cited by examiner

*Primary Examiner* — John M Cooney
(74) *Attorney, Agent, or Firm* — Erson IP (Nelson IP)

(57) ABSTRACT

The present invention provides a method for preparing hydrophilic polymer foam. The method comprises a step of providing an isocyanate functionalized prepolymer (A) and a step of foaming and curing the prepolymer (A). The prepolymer (A) is prepared by reacting diisocyanate (A1) and polyether polyol (A2), wherein the diisocyanate (A1) is selected from any one and a combination of 1,4-butyl diisocyanate (BDI), lysine diisocyanate (LDI) and 1,5-pentyl diisocyanate (PDI); the polyether polyol (A2) is a copolymer of ethylene oxide (EO) and propylene oxide (PO) and/or butylene oxide (BO); the ethylene oxide has a weight percentage of about 50%-100% in the polyether polyol, and has an OH functionality degree of 3-6, a hydroxyl value of about 21 mg KOH/g-168 mg KOH/g and a number-average molecular weight of about 1000 g/mol to about 8000 g/mol; and NCO content in the prepolymer (A) is 1%-10%.

8 Claims, 5 Drawing Sheets

HYDROPHILIC AND BIOLOGICALLY SAFE POLYMER FOAM AS WELL AS PREPARATION METHOD AND APPLICATION THEREOF

CROSS-REFERENCE TO RELATED APPLICATIONS

This application is a continuation of International Patent Application No. PCT/PCN2016/092823 with a filing date of Aug. 2, 2016, designating the United States, now pending, and further claims priority to Chinese Patent Application No. 201510472222.8 with a filing date of Aug. 4, 2015. The content of the aforementioned applications, including any intervening amendments thereto, are incorporated herein by reference.

TECHNICAL FIELD

The present invention relates to hydrophilic polymer foam, and particularly relates to a preparation method of hydrophilic polyurethane foam with biological safety, a product prepared by the method and an application of the product.

BACKGROUND OF THE PRESENT INVENTION

Isocyanate is a main raw material for synthesis of polyurethane, and can be generally divided into an aliphatic category and an aromatic category. Although many types of the isocyanate are introduced in literatures, only the above two categories are actually applied. At present, there are two main types of polyurethane dressing, that is, one polyurethane dressing type taking aromatic isocyanates as raw materials, such, as toluene diisocynate (TDI) and diphenylmethane diisocyanate (MDI); and the other polyurethane dressing type taking aliphatic diisocyanates as raw materials, such as hexamethylene diisocyanate (HDI), dicyclohexylmethane diisocyanate (HMDI) and isophorone diisocyanate (IPDI).

A U.S. Pat. No. 7,777,091 proposes a polyurethane system taking the toluene diisocynate (TDI) and the isophorone diisocyanate (IPDI) as main raw materials, wherein a polyether component is an ethylene oxide (EO)/propylene oxide (PO) tri-functional copolymer with high EO content. However, the material may produce toluenediamine (TDA), diphenylmethane toluene diamine (MDA) and other aromatic diamines in a degradation process when used in a medical dressing. Lots of toxicity experiments prove that the TDA and the MDA are strong cancerogenic substances capable of inducing gene mutation. Therefore, the polyurethane taking the aromatic isocyanates as the raw materials is not an ideal safety material.

A United States patent US 20110184080 (with an application number of U.S. Ser. No. 13/003,205) discloses a method of preparing a prepolymer from hexamethylene diisocyanate (HDI) and a polyether with high EO content, synthesizing hydrophilic isocyanate from a tri-functional HDI tripolymer and a mono-functional polyoxyethylene alcohol, and enabling a mixture of the prepolymer and the hydrophilic isocyanate to react under a combined action of water, a catalyst and a surfactant to produce a hydrophilic polyurethane foam material. The principal isocyanate is aliphatic diisocyanate such as the HDI. Hexamethylenediamine (HDA) exists in a degradation product of such a polyurethane material. Although the substance is not carcinogenic aromatic diamine, the substance is still not a substance existing in a human body, and safety should be further verified. Meanwhile, a catalyst and other metal salts thereof should be added to serve as foaming assistants in a material preparation process, otherwise an ideal foam material cannot be obtained, and foam may suffer from expected intense contraction after foaming.

SUMMARY OF PRESENT INVENTION

In order to solve a problem existing in an existing polyurethane foam material that a degradation product is poor in safety, the inventor discovers that, by virtue of a method disclosed herein, a polyurethane foam material prepared by taking any one or a combination of lysine diisocyanate (LDI), 1,4-butyl diisocyanate (BDI) and 1,5-pentyl diisocyanate (PDI) as an isocyanate raw material can provide a medical hygiene product with high biological safety.

The inventor is further surprised to find that, in a process of preparing the polyurethane foam material by taking any one or a combination of the LDI the BDI and the PDI as the isocyanate raw material even if an extra catalyst or any other extra metal salt is not added, a hydrophilic polyurethane foam material may also be obtained, and is high in porosity, lightweight, high in water absorption rate and particularly suitable to serve as a wound dressing, an incontinence product and a beauty product. Moreover, the prepared polyurethane foam material has excellent human contact safety, and the safety of the material is much higher than descriptions in existing market products and existing patents.

In one aspect, the present invention provides a method for preparing hydrophilic polyurethane foam. The method comprises a step of providing an isocyanate functionalized prepolymer (A) and a step of foaming and curing the prepolymer (A). The prepolymer (A) is prepared by reacting diisocyanate (A1) and polyether polyol (A2), wherein the diisocyanate (A1) is selected from any one and a combination of 1,4-butyl diisocyanate (BDI), lysine diisocyanate (LDI) and 1,5-pentyl diisocyanate (PDI); the polyether polyol (A2) is a copolymer of ethylene oxide (EO) and propylene oxide (PO) and/or butylene oxide (BO); the ethylene oxide has a weight percentage of about 50%-100% in the polyether polyol, and has an OH functionality degree of 3-6, a hydroxyl value of about 21 mg KOH/g-168 mg KOH/g and a number-average molecular weight of about 1000 g/mol-8000 g/mol and NCO content in the prepolymer (A) is 1%-10%.

In another aspect, the present invention provides a method for preparing hydrophilic polyurethane foam. The method further comprises a of at least partially removing unreacted diisocyanates (A1) after a step of providing an isocyanate functionalized prepolymer (A).

In another aspect, the present invention provides a method for preparing hydrophilic polyurethane foam. The method further comprises a step of mixing a prepolymer (A) with lysine triisocyanate (LTI) (B) before a step of foaming and curing.

In another aspect, the present invention provides a method for preparing hydrophilic polyurethane foam. The method further comprises a step of mixing a prepolymer (A) with modified polyfunctional isocyanate (C) before a step of foaming and curing, wherein the modified polyfunctional isocyanate (C) contains a polymer of the lysine triisocyanate (LTI) (B) and mono-functional polyoxyethylene (C2) with a number-average molecular weight of 200 g/mol to 2000 g/mol.

In another aspect, the present invention provides a method for preparing hydrophilic polyurethane foam. The method further comprises a step of mixing a prepolymer (A) with the lysine triisocyanate (LTI) (B) and the modified polyfunctional isocyanate (C) before a step of foaming and curing, wherein the modified polyfunctional isocyanate (C) contains a polymer of the lysine triisocyanate (LTI) (B) and monofunctional polyoxyethylene (C2) with a number-average molecular weight of 200 g/mol to 2000 g/mol.

In another aspect, the present invention provides a method for preparing hydrophilic polyurethane foam. No catalyst is used in the method.

In another aspect, the present invention provides a method for preparing hydrophilic polyurethane foam. No metal salt additive is used in the method.

DETAILED DESCRIPTION OF PREFERRED EMBODIMENTS

Figure 1:
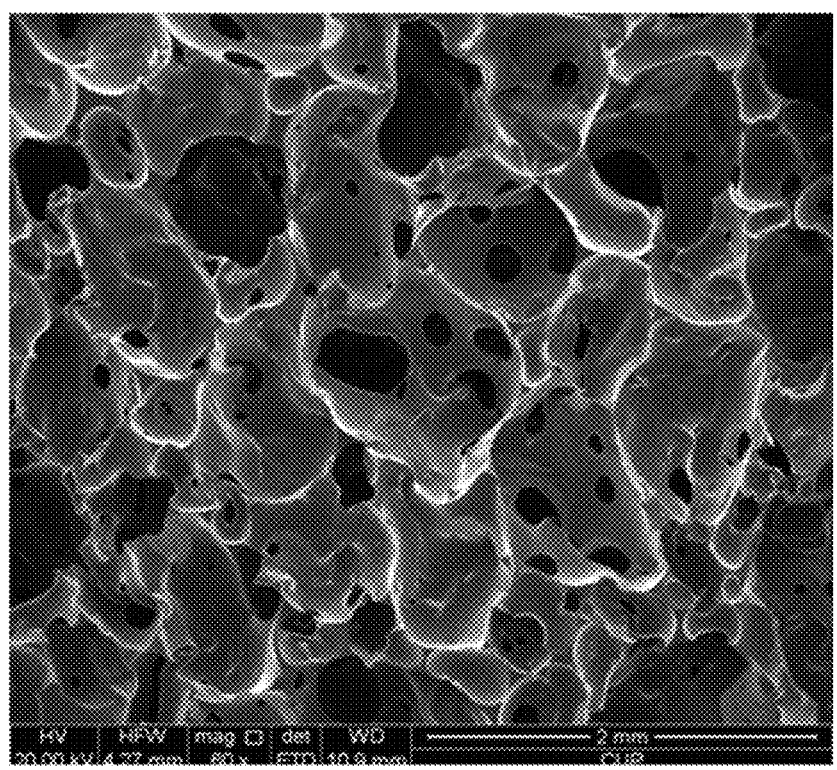
FIG. 1 is an electronic microscope photograph of foam obtained by foaming in a BDI system.

Embodiments of the present invention are described below in detail to better understand, illustrate and realize the present invention.

Isocyanate prepolymer (A)

The isocyanate prepolymer (A) is prepared by reacting excessive diisocyanate (A1) and polyether polyol (A2).

Diisocyanate (A1)

The diisocyanate (A1) may be any one and a combination of 1,4-butyl diisocyanate (BDI), lysine diisocyanate (LDI) and 1,5-pentyl diisocyanate (PDI).

A degradation product of a polyurethane foam material prepared by taking lysine diisocyanate (LDI) as an isocyanate raw material is an amino acid, that is lysine, in a human body does not cause any inflammation, and is friendly to a cell interface, small in non-biospecific effect, and the like.

A degradation product of a polyurethane material prepared by taking the 1,4-butyl diisocyanate (BDI) as an isocyanate raw material is 1,4-diaminobutane, and can be absorbed by the human body. The 1,4-diaminobutane is also called putrescine, and is an amino acid degradation product of proteins in a living organism or a dead organism. A molecular formula of the putrescine is $NH_2(CH_2)_4NH_2$. In an organism, orinithinedecarboxylase can be degraded under an action of ornithine decarboxylase to produce a small amount of putrescine. Poly-amino compounds (the putrescine is one poly-amino compound with the simplest structure therein) are a kind of growth factors essential in a cell division process. The putrescine widely exists as a normal component of the living body, and can be found in each cell. It is believed that, a pH value of cells is controlled by increasing or decreasing a content level of the putrescine in the compounds.

A degradation product of a polyurethane material prepared by taking the 1,5-pentyl diisocyanate (PDI) as an isocyanate raw material is 1,5-diaminopentane, and the 1,5-diaminopentane is also called pentamethyiene diamine, has a structural formula, of $NH_2(CH_2)_5NH_2$, is produced by carrying out a decarboxylic reaction on lysine under an effect of decarboxylase during protein putrefaction, and is a normal component existing in organisms widely. The pentamethylene diamine is a compound which is produced by proteolysis during decaying of animal body tissues and has a putrid flavor, is slurry liquid at a normal temperature and may be solidified and crystallized by deep refrigeration. Actually, such a diamine is not only related to putrefaction. A small amount of pentamethylene diamine may also be produced by the organisms during metabolization. The pentamethylene diamine is part of the reason causing a special smell of urine and seminal fluid.

Polyether polyol (A2)

The polyether polyol (A2) may be a copolymer of ethylene oxide (EO) and propylene oxide (PO) and/or butylene oxide (BO), preferably a copolymer of the ethylene oxide (EO) and the propylene oxide (PO). Moreover, the ethylene oxide has a weight percentage of about 50%-100% in the polyether polyol (A2), preferably greater than 80% and less than 100%.

A number-average molecular weight of the polyether polyol (A2) is typically in a range from about 1000 g/mol to about 8000 g/mol, preferably in a range from about 3000 g/mol to about 5000 g/mol.

The polyether polyol (A2) has an OH functionality degree of 3-6, preferably an OH functionality degree of 3-4, and has a hydroxyl value of about 168 g/mol to about 21 g/mol, preferably about 56 mgKOH/g to 33 mgKOH/g.

The polyether polyol (A2) is a copolymer formed by taking polyhydric alcohols or amines as initiators. Appropriate initiators may include glycerin, trimethylolpropane (TMP), sorbitol, pentaerythritol, triethanolamine, ammonia or ethidene diamine, preferably the glycerin and the trimethylolpropane (TMP), and further preferably the glycerin.

A molar ratio of the diisocyanate (A1) to the polyether polyol (A2) is generally (1-20):1 preferably (1-10):1 and more preferably (4-7):1.

NCO content in the isocyanate functionalized prepolymer (A) is 1-10%, preferably 3-9%, and more preferably 4-8%. A value of the NCO content is determined according to a "method for determining isocyanato content in polymethylene polyphenyl isocyanate" in GB/T 12009.4-1989.

Unreacted excessive diisocyanates in the prepolymer (A) may be removed through thin film evaporation and other methods, so that the NCO content in the isocyanate functionalized prepolymer (A) is decreased to be below 3%, or further decreased to be below 2%.

The prepolymer (A) has a number-average molecular weight from about 1000 g/mol to about 8000 g/mol, and preferably a number-average molecular weight from about 3000 g/mol to about 5000 g/mol.

A reaction between the isocyanate (A1) and the polyether polyol (A2), is generally carried out at a temperature of about 50° C.-100° C., and preferably about 70° C.-90° C.

The reaction between the diisocyanate (A1) and the polyether polyol (A2) may also be carried out even if conventional urethanation catalysts such as tin compounds, zinc compounds, amines, guanidine or amidine are not used, and economic production efficiency is achieved.

A stabilizer may be added into a reaction system to increase stability of a diisocyanate monomer. For example, acidic or alkylated stabilizers may be added, such as benzoyl chloride, isophthalyl chloride, menthylbenzene sulfonate, chloropropionic acid, hydrochloric acid or an antioxidant, e.g., di-tert-butyl-methylphenol or tocopherol.

The method further comprises a step of mixing the prepolymer (A) with lysine triisocyanate (LTI) (B) before a step of foaming and curing. A definition of the prepolymer (A) is as mentioned above. The prepolymer (A) is a prepolymer formed by reacting lysine diisocyanate (LDI) and the polyether polyol (A2). A weight ratio of the prepolymer (A) to the lysine triisocyanate (LTI) (B) is about 10:1 to about 40:1, and preferably about 20:1 to about 25:1.

The method may further comprise a step of mixing the prepolymer (A) with modified polyfunctional isocyanate (C) before a step of foaming and curing. The modified polyfunctional isocyanate (C) contains a prepolymer formed by reacting the lysine triisocyanate (LTI) (B) and mono-functional polyoxyethylene (C2) with a number-average molecular weight of about 200 g/mol to about 2000 g/mol, and a molar ratio of the lysine triisocyanate (LTI) (B) to the mono-functional polyoxyethylene (C2) is about 1:1 to about 10:1. A weight ratio of the prepolymer (A) to the modified polyfunctional isocyanate (C) is about 1:1 to about 50:1, and preferably about 1:1 to about 10:1.

The method may further comprise a step of mixing the prepolymer (A) with the lysine triisocyanate (LTI) (B) and the modified polyfunctional isocyanate (C) before a step of foaming and curing. The modified polyfunctional isocyanate (C) contains a polymer of the lysine triisocyanate (LTI) (B) and the mono-functional polyoxyethylene (C2) with the number-average molecular weight of about 200 g/mol to about 2000 g/mol, and a molar ratio of the lysine triisocyanate (LTI) (B) to the mono-functional polyoxyethylene (C2) is about 1:1 to about 10:1. An addition amount of the prepolymer (A), the lysine triisocyanate (LTI) (B) and the modified polyfunctional isocyanate (C) is about 100 weight parts of the prepolymer (A), 0-10 weight parts of the lysine triisocyanate (LTI) (B) and 0-20 weight parts of the modified polyfunctional isocyanate (C).

Foaming agent (D)

The foaming agent may be selected from water, dichlorofluoroethane (CFC-141b) and the like, and preferably the water.

Cross-linking agent (E)

The cross-linking agent may be selected from polyhydroxy compounds with more than two functionality degrees, and includes but not limited to glycerin, trimethylolpropane, pentaerythritol, sorbitol and the like, as well as any mixture thereof. Preferably, polyhydric alcohols with more than 2 functionality degrees serve as the cross-linking agent, and preferably, glycerin serves as the cross-linking agent.

Catalyst (F)

Catalysts may be used or not used in a foaming process. When the catalysts are adopted, formation of urethane may be accelerated. The catalysts are typically known compounds in the technical field of polyurethane synthesis, and are preferably selected from compounds for catalyzing reactive metals, amines, amidines and guanidines, such as stannous octoate, tin acetate, zinc caprylate, dibutyltin dilaurate (DBTL), 1,8-diazabicycloundecane-7-ene (DBU), 1,5-diazabicyclo[4.3.0] nonylene-5 (DBN), 1,4-diazabicyclo[3.3.0] octylene-4 (DBO), N-ethyl morpholine (NEM), triethylenediamine (DABCO), pentamethyl guanidine (PMG), tetramethyl guanidine (TMG), cyclotetramethyl guanidine (TMGC), n-decyl tramethyl guanidine (TMGD), n-dodecyl tramethyl guanidine (TMGDO), dimethyl aminoethyl tramethyl guanidine (TMGN), 1,1,4,4,5,5-hexamethyl isobiguanide (HMIB), phenyl tetramethyl guanidine (TMGP) and hexamethylene octamethyl guanidine (HOBG).

Further preferably, the catalysts are amines, amidines, guanidines or mixtures thereof. Particularly preferably, any catalyst is not added into the present invention.

Surfactant (G)

Surfactants may be added for improving formation, stability or performance of foam. The surfactants may be anionic surfactants, cationic surfactants, ampholytic surfactants or nonionic surfactants and mixtures thereof. For example, polyether modified silicone oil may be selected, such as Evonik B8715(Tegostab® B 8715), Evonik B8870 (TEGOSTAB® B 8870), Evonik 0-501, Evonik B8871 (Tegostab® B8871), Evonik B8409(Tegostab® B8409), Evonik B8948(Tegostab® B8948), Evonik B8738 (Tegostab® B8738), Evonik B8460(Tegostab® B8460) and the like.

In some embodiments, the components (A) to (S) may be typically used at the following doses:

100 weight parts of the isocyanate functionalized prepolymer (A)

0-100 weight parts of the water (D)

0-40 weight parts of the cross-linking agent (E)

0-1 weight part of the catalyst (F)

0-3 weight parts of the surfactant (G).

A preferred range of the doses of the above substances is that:

100 weight parts of the isocyanate functionalized prepolymer (A)

10-60 weight parts of the water (D)

0-20 weight parts of the cross-linking agent (E)

0 weight part of the catalyst (F)

1-2 weight parts of the surfactant (G).

In some other embodiments, the components (A) to (G) may be typically used at the following doses;

100 weight parts of the isocyanate functionalized prepolymer (A)

0-10 weight parts of the, lysine triisocyanate (LTI) (B)

0-100 weight parts of the water (D)

0-40 weight parts of the cross-linking agent (E)

0-1 weight part of the catalyst (F)

0-2 weight parts of the surfactant (G).

A preferred range of the doses of the above substances is that:

100 weight parts of the isocyanate functionalized prepolymer (A)

1-5 weight parts of the lysine triisocyanate (LTI) (B)

10-50 weight parts of the water (D)

0-20 weight parts of the cross-linking agent (E)

0 weight part of the catalyst (F)

0-1.5 weight parts of the surfactant (G).

In some other embodiments, the components (A) to G) may be typically used at the following doses:

100 weight parts of the isocyanate functionalized prepolymer (A)

0-100 weight parts of modified polyfunctional isocyanate (C)

0-100 eight parts of the water (D)

0-40 weight parts of the cross-linking agent (E)

0-1 weight part of the catalyst (F)

0-2 weight parts of the surfactant (G).

A preferred range of the doses of the above substances is that:

100 weight parts of the isocyanate functionalized prepolymer (A)

10-80 weight parts of modified polyfunctional isocyanate (C)

10-50 weight parts of the water (D)

0-20 weight parts of the cross-linking agent (E)

0 weight part of the catalyst (F)
0-1 weight part of the surfactant (G).

In some other embodiments, the components (A) to (G) ay be typically used at the following doses:
100 weight parts of the isocyanate functionalized prepolymer (A)
0-10 weight parts of the lysine triisocyanate (LTI) (B)
0-100 weight pans of the modified polyfunctional isocyanate (C)
0-100 weight parts of the water (D)
0-40 weight parts of the cross-linking agent (E)
0-1 weight part of the catalyst (F)
0-2 weight parts of the surfactant (G).

A preferred range of the doses of the above substances is that:
100 weight parts of the isocyanate functionalized prepolymer (A)
2-8 weight parts of the lysine triisocyanate (LTI) (B)
0-80 weight parts of the modified polyfunctional isocyanate (C)
10-50 eight parts of the water (D)
0-20 weight parts of the cross-linking agent (E)
0 weight part of the catalyst (F)
0-1 weight part of the surfactant (G).

In the method for preparing the polyurethane foam disclosed herein, the components (A), (D), (E) and (G) are mixed with optional components (B), (C) and (F) in a random order, and the mixture is foamed and then cured.

The polyurethane foam prepared by the method has flexibility, can be used as a wound dressing, an incontinence device or a cosmetic and other applications, and is particularly directly contacted with wounds and skin on human or animal skin.

The polyurethane foam has a relatively low density, and the density is about 0.01 g/cm$^3$ to about 0.50 g/cm$^3$, and preferably about 0.10 g/cm$^3$ to about 0.20 g/cm$^3$ (determined according to a GB/T 6343-2009_method.

A physiological saline absorption rate of the polyurethane foam is typically in a range from about 100% to about 3000%, preferably in a range from about 500% to about 2000%, preferably in a range from about 1000% to about 1300%, and most preferably in a range from more than 800% to about 1500% (determined according to a GB/T 8810-2005 method).

Figure 3:
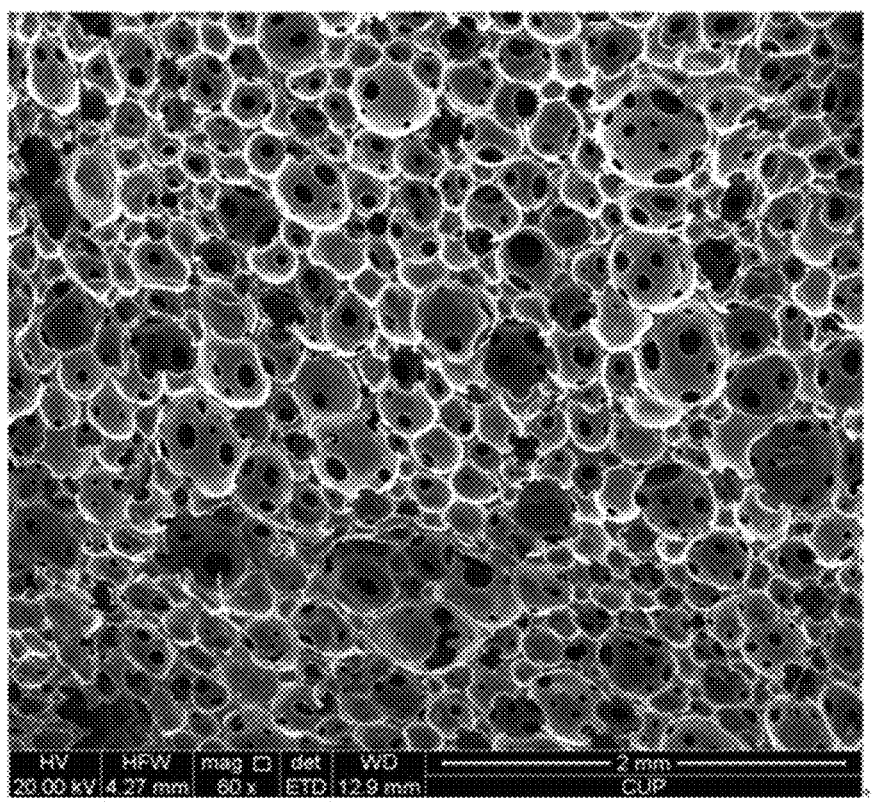
FIG. 3 is an electronic microscope photograph of foam obtained by foaming in an LDI and LTI system.
Figure 4:
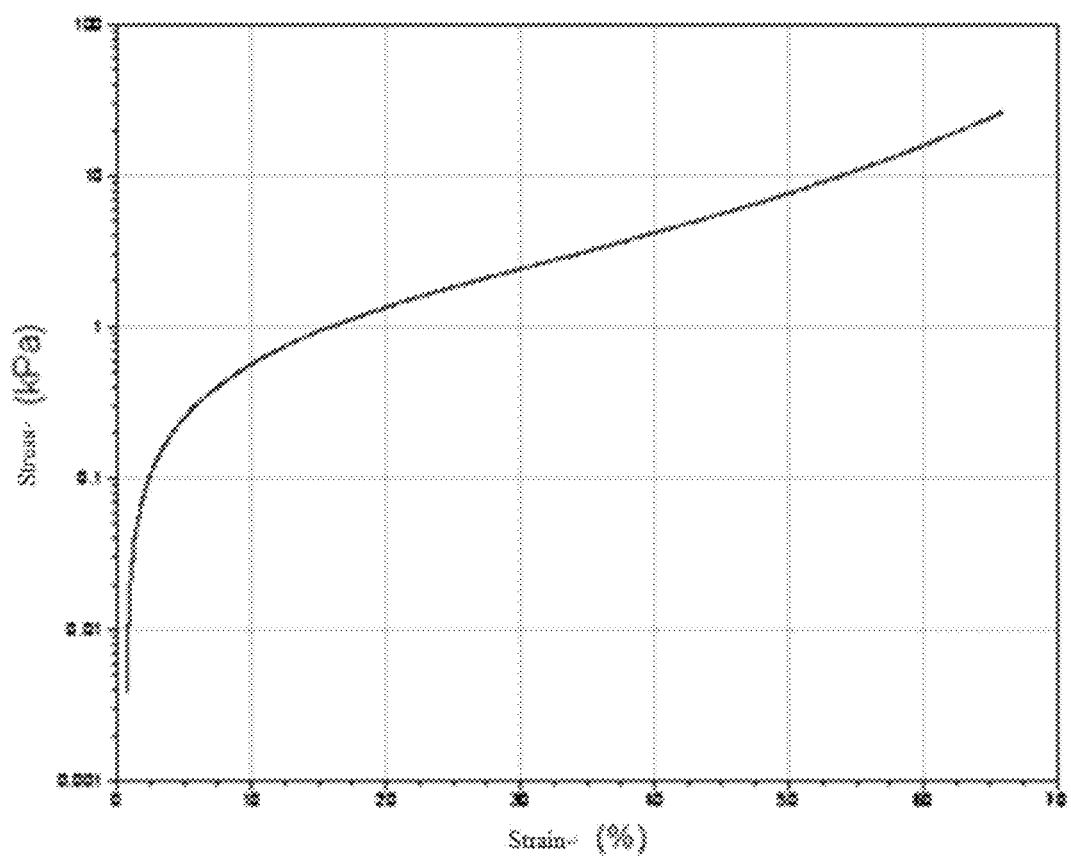
FIG. 4 is a stress-strain curve of foam obtained by foaming in a BDI system.
Figure 5:
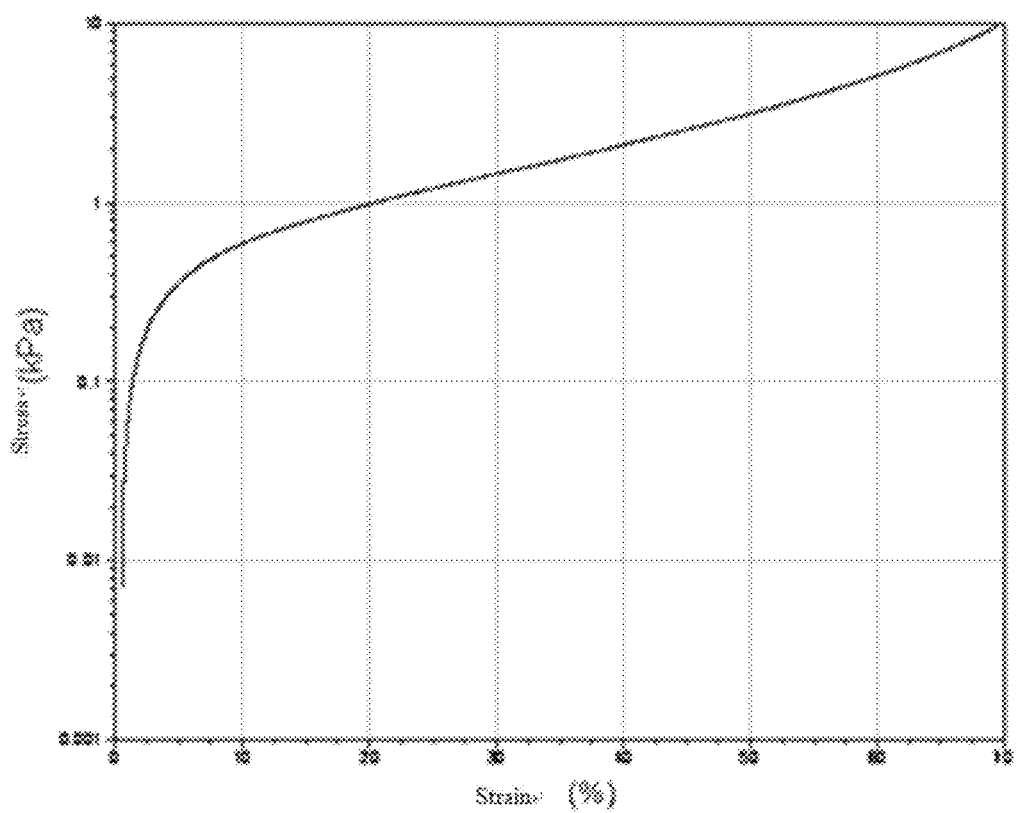
FIG. 5 is a stress-strain carve of foam obtained by foaming in an LDI system.

The polyurethane foam has an excellent comfort compression curve (see FIG. 3 and FIG. 4).

Preparation of isocyanate functionalized prepolymer (A)

Embodiment 1

Preparation of Prepolymer 1 steps: adding 40 g of 1,4-butyl diisocyanate (BDI) and 200 g of polyether polyol ZS-3602 with 3 OH functionality degrees, EO content of 80%, a hydroxyl value of 35 mg KOH/g and a number-average molecular weight of 4800 into a 3-mouth flask, heating at 70° C. and stirring for 7 hours, stopping the reaction when NCO content reaches a theoretical value of 7%, and cooling for later use, wherein the NCO is determined according to a national standard GB/T 12009.4-1989.

Embodiment 2

Preparation of Prepolymer 2 steps: adding 50 g of lysine diisocyanate (LDI) and 150 g of polyether polyol ZS-3602, with 3 OH functionality degrees, EO content of 80%, a hydroxyl value of 35 mg KOH/g and a number-average molecular weight of 4800 into a 3-mouth flask, heating at 70° C. and stirring for 7 hours, stopping the reaction when NCO content reaches a theoretical value of 7%, and cooling for later use, wherein the NCO is determined according to a national standard GB/T 12009.4-1989.

Embodiment 3

Preparation of Polyurethane Foam 1 steps: stirring 24 g of prepolymer 1, 10 g of water, 5 g of glycerin and 0.07 g of a surfactant B8460 at a revolution speed of 4000 rmp for 10 seconds, then rapidly pouring the mixture into a beaker, and freely foaming at 40° C.

The prepared polyurethane foam has the following characteristics:
sample density: 0.18 g/cm$^3$ (determined according to a GB/T 6343-2009 method)
water absorption rate 1200% (determined according to a GB/T 8810-2005 method)

As shown in FIG. 1, a foam cell diameter is in a range from 400 μm to 600 μm, and open pores of 100 μm to 200 μm are formed in pore foam cells. In such a structure, on one hand, liquid absorption is facilitated; and on the other hand, the open pores effectively prevent foam from collapsing in the foaming process.

As shown in a stress-strain curve in FIG. 3, the polyurethane foam has excellent comfortable compression performance.

Embodiment 4

Preparation of Polyurethane Foam 2 steps: stirring 24 g of a prepolymer 2, 10 g of water, 5 g of glycerin and 0.07 g of surfactant B8460 at a revolution speed of 4000 rmp for 10 seconds, then rapidly pouring the mixture into a beaker, and freely foaming at 40° C.

The prepared polyurethane foam has the following characteristics:
sample density: 0.17 g/cm$^3$ (determined according to a GB/T 6343-2009 method)
water absorption rate 1100% (determined according to a GB/T 8810-2005 method)

Figure 2:
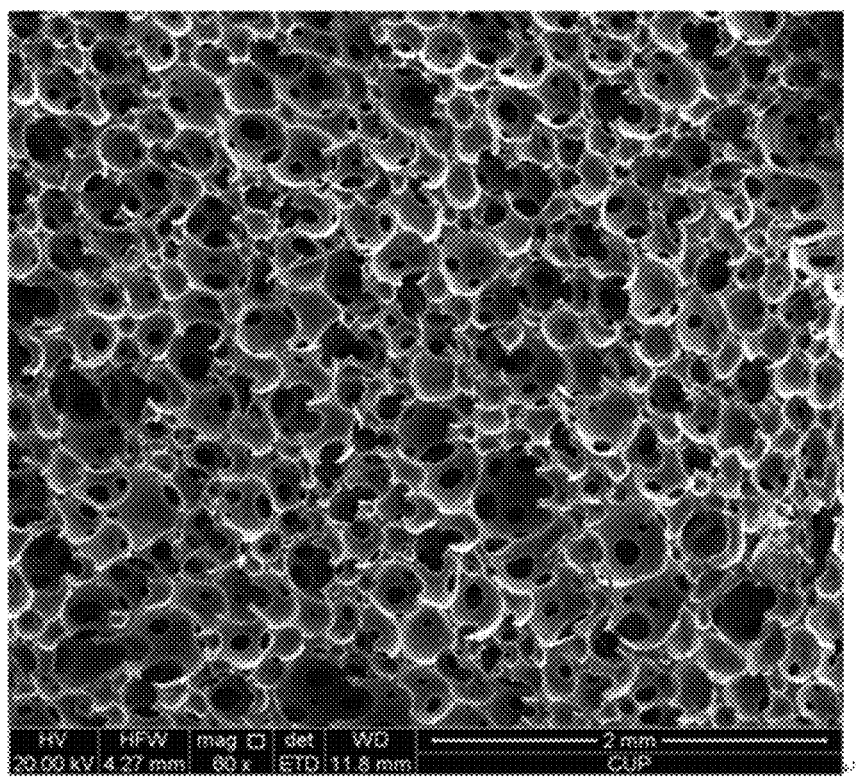
FIG. 2 is an electronic microscope photograph of foam obtained by foaming in an LDI system.

As shown in FIG. 2, a foam cell diameter is in a range from 200 μm to 400 μm, and open pores of 50 μm to 100 μm, are formed in pore foam cells. On one hand, liquid absorption is facilitated; and on the other hand, the open pores effectively prevent foam from collapsing in the foaming process. As shown in a stress-strain curve in FIG. 4, the polyurethane foam has excellent comfortable compression performance.

Embodiment 5

Preparation of Polyurethane Foam 3 steps: stirring 22 g of a prepolymer 2, 1.5 g of trifunctional L-lysine triisocyanate (LTI), 10 g of water, 5 g of glycerin and 0.07 g of surfactant B8460 at a revolution speed of 4000 rmp for 10 seconds, then rapidly pouring the mixture into a beaker, and freely foaming at 40° C.

The prepared polyurethane foam has the following characteristics:

sample density: 0.15 g/cm³ (determined according to a GB/T 6343-2009 method)

water absorption rate 1100% (determined according to GB/T 8810-2005 method)

As shown in FIG. 3, a foam cell diameter is in a range from 200 µm to 400 µm, and open pores of 50 µm to 100 µm are formed in pore foam cells. On one hand, liquid absorption is facilitated; and on the other hand, the open pores effectively prevent foam from collapsing in the foaming process.

Reference Embodiment 1

Preparation of Polyurethane Foam 4 steps: stirring 24 g of a prepolymer 1, 10 g of water, 5 g of glycerin, 0.07 g of surfactant B8460 and 0.05 g of catalyst DBU at a revolution speed of 4000 rmp for 10 seconds, then rapidly pouring the mixture into a beaker, and freely foaming at 40° C.

A sample cannot be normally formed.

Reference Embodiment 2

Preparation of Polyurethane Foam 5 steps: stirring 24 g of prepolymer 2, 10 g of water, 5 g of glycerin, 0.07 g of surfactant B8460 and 0.05 g of catalyst DBU at a revolution speed of 4000 rmp for 10 seconds, then rapidly pouring the mixture into a beaker, and freely foaming at 40° C.

A sample cannot be normally formed.

Reference Embodiment 3

Preparation of Polyurethane Foam 6 steps: mixing 22 g of prepolymer 2, 1.5 g of tri-functional L-lysine triisocyanate, 10 g of water, 5 g of glycerin, 0.07 g of surfactant B8460 and 0.05 g of catalyst DBU, stirring at a revolution speed of 4000 rmp for 10 seconds, then rapidly pouring the mixture into a beaker, and freely foaming at 40° C.

A sample cannot be normally formed.

We claim:

1. A method for preparing novel hydrophilic polymer foam, comprising the following steps:
   providing an isocyanate functionalized prepolymer (A), wherein
   the prepolymer (A) being obtained by reacting diisocyanate (A1) and polyether polyol (A2), wherein
   the diisocyanate (A1) is selected from any one and a combination of 1,4-butyl diisocyanate (BDI), lysine diisocyanate (LDI) and 1,5-pentyl diisocyanate (PDI);
   the polyether polyol (A2) is a copolymer of ethylene oxide (EO)) and propylene oxide (PO) and/or butylene oxide (BO); the ethylene oxide has a weight percentage of about 50%-100% in the polyether polyol, and has an OH functionality degree of 3-6, a hydroxyl value, of about 21 mg KOH/g-168 mg KOF/g and a number-average molecular weight of about 1000 g/mol-8000 g/mol;
   NCO content in the prepolymer (A) is 1%-10%; and
   foaming and curing the prepolymer (A);
   wherein the method further comprises a step of mixing a prepolymer (A) with a modified polyfunctional isocyanate (C) before the step of foaming and curing, wherein the modified polyfunctional isocyanate (C) contains a polymer of a lysine triisocyanate (LTI) (B) and a mono-functional polyoxyethylene (C2) with a number-average molecular weight of about 200 g/mol to about 2000 g/mol.

2. The method for preparing hydrophilic polyurethane foam according to claim 1, wherein the method further comprises a step of at least partially removing unreacted diisocyanates (A1) after a step of providing the isocyanate functionalized prepolymer (A).

3. The method for preparing hydrophilic polyurethane foam according to claim 1, wherein the polyether polyol (A2) takes polyhydric alcohols or amines as initiators; and the ethylene oxide in the polyether polyol (A2) has a weight percentage greater than 80% and less than 100%.

4. The method for preparing hydrophilic polyurethane foam according to claim 1 wherein a number-average molecular weight of the polyether polyol (A2) is about 3000 g/mol to about 6000 g/mol, and a hydroxyl value is about 56 mgKOH/g to 28 mgKOH/g.

5. A method for preparing novel hydrophilic polymer foam, comprising the following steps:
   providing an isocyanate functionalized prepolymer (A), wherein
   the prepolymer (A) being obtained by reacting diisocyanate (A1) and polyether polyol (A2), wherein
   the diisocyanate (A1) is selected from any one and a combination of 1,4-butyl diisocyanate (BDI), lysine diisocyanate (LDI) and 1,5-pentyl diisocyanate (PDI);
   the polyether polyol (A2) is a copolymer of ethylene oxide (EO)) and propylene oxide (PO) and/or butylene oxide (BO); the ethylene oxide has a weight percentage of about 50%-100% in the polyether polyol, and has an OH functionality degree of 3-6, a hydroxyl value, of about 21 mg KOH/g-168 mg KOF/g and a number-average molecular weight of about 1000 g/mol-8000 g/mol;
   NCO content in the prepolymer (A) is 1%-10%; and
   foaming and curing the prepolymer (A);
   wherein the method further comprises a step of mixing a prepolymer (A) with lysine triisocyanate (LTI) (B) and a modified polyfunctional isocyanate (C) before the step of foaming and curing, wherein the modified polyfunctional isocyanate (C) contains a polymer of a lysine triisocyanate (LTI) (B) and a mono-functional polyoxyethylene (C2) with a number-average molecular weight of about 200 g/mol to about 2000 g/mol.

6. The method for preparing hydrophilic polyurethane foam according to claim 5, wherein the method further comprises a step of at least partially removing unreacted diisocyanates (A1) after a step of providing the isocyanate functionalized prepolymer (A).

7. The method for preparing hydrophilic polyurethane foam according to claim 5, wherein the polyether polyol (A2) takes polyhydric alcohols or amines as initiators;
   and the ethylene oxide in the polyether polyol (A2) has a weight percentage greater than 80% and less than 100%.

8. The method for preparing hydrophilic polyurethane foam according to claim 5 wherein a number-average molecular weight of the polyether polyol (A2) is about 3000 g/mol to about 6000 g/mol, and a hydroxyl value is about 56 mgKOH/g to 28 mgKOH/g.

* * * * *